(12) United States Patent
Yoshimura et al.

(10) Patent No.: US 8,408,056 B2
(45) Date of Patent: Apr. 2, 2013

(54) EGR RATIO MEASURING DEVICE

(75) Inventors: Tomoshi Yoshimura, Kyoto (JP); Masaru Miyai, Kyoto (JP)

(73) Assignee: Horiba, Ltd., Kyoto (JP)

( * ) Notice: Subject to any disclaimer, the term of this patent is extended or adjusted under 35 U.S.C. 154(b) by 219 days.

(21) Appl. No.: 12/976,372

(22) Filed: Dec. 22, 2010

(65) Prior Publication Data

US 2011/0154891 A1 Jun. 30, 2011

(30) Foreign Application Priority Data

Dec. 25, 2009 (JP) ................................. 2009-295710

(51) Int. Cl.
*G01M 15/10* (2006.01)
(52) U.S. Cl. .................................................. 73/114.74
(58) Field of Classification Search ................. 73/114.74
See application file for complete search history.

(56) References Cited

U.S. PATENT DOCUMENTS

| | | | | |
|---|---|---|---|---|
| 5,368,005 A * | 11/1994 | Kako | ....................... | 123/568.16 |
| 5,964,820 A * | 10/1999 | Miwa et al. | ................... | 701/108 |
| 6,658,345 B2 * | 12/2003 | Miller | ........................... | 701/108 |
| 6,886,336 B2 * | 5/2005 | Super et al. | .................. | 60/605.2 |
| 7,007,680 B2 * | 3/2006 | Tussing et al. | ........... | 123/568.12 |
| 7,389,771 B2 * | 6/2008 | Andrews et al. | ......... | 123/568.22 |
| 7,715,976 B1 * | 5/2010 | Xiao et al. | ..................... | 701/108 |
| 2003/0114978 A1 * | 6/2003 | Rimnac et al. | ................ | 701/108 |
| 2003/0192516 A1 * | 10/2003 | Brunemann et al. | ...... | 123/568.12 |
| 2009/0132153 A1 * | 5/2009 | Shutty et al. | .................. | 701/108 |
| 2010/0326408 A1 * | 12/2010 | Clarke et al. | ............. | 123/568.21 |

FOREIGN PATENT DOCUMENTS

| JP | 2003-172700 | 6/2003 |
|---|---|---|
| JP | 2008-069690 | 3/2008 |

OTHER PUBLICATIONS

Engine emission measurement handbook p. 132-p. 133 (Sankaido Publishing Co., Ltd.), 2006.

\* cited by examiner

*Primary Examiner* — Freddie Kirkland, III
(74) *Attorney, Agent, or Firm* — Brooks Kushman P.C.

(57) ABSTRACT

An EGR ratio measuring device comprises a pair of nondispersive infrared gas analyzers that correct a water influence and measure a concentration of $CO_2$ in a gas containing water, an intake air introduction line that is connected to an intake air pipe of an internal combustion engine and introduces a part of the intake air into one nondispersive infrared gas analyzer without removing the water, an exhaust gas introduction line that is connected to an exhaust gas pipe of the internal combustion engine and introduces a part of the exhaust gas into the other nondispersive infrared gas analyzer without removing the water, and a temperature adjusting mechanism that keeps a temperature of whole of the introduction lines and a temperature of the nondispersive infrared gas analyzers so as not to condense dew.

2 Claims, 4 Drawing Sheets

EGR RATIO MEASURING DEVICE

CROSS-REFERENCE TO RELATED APPLICATIONS

This application claims the benefit of JP 2009-295710, filed Dec. 25, 2009. The disclosure of which is incorporated in its entirety by reference herein.

FIELD OF THE ART

This invention relates to an EGR ratio measuring device that measures an EGR ratio in an internal combustion engine having an exhaust gas recirculation system (EGR system), namely, a ratio of a gas recirculation amount from an exhaust gas pipe to an intake air amount including the recirculation amount.

BACKGROUND ART

The EGR ratio measuring device is so arranged that a reflux flow channel (R) connecting an exhaust gas pipe (EXT) with an intake air pipe (INT) of an internal combustion engine (EG) is provided as shown in FIG. 4 so that a combustion temperature is lowered by refluxing the exhaust gas to the intake air and eventually reduces $NO_X$. As shown in the patent document 1, an EGR ratio is known as a parameter to control the refluxing amount by an EGR valve (V) and to optimize combustion of the internal combustion engine (EG).

The EGR ratio is a ratio of the gas recirculation amount from the exhaust gas pipe (EXT) to the intake air amount including the recirculation amount. A $CO_2$ concentration at an intake air side and a $CO_2$ concentration at an exhaust gas side are measured and the EGR ratio can be calculated from the measured value of the $CO_2$ concentration by the use of the following equation (1).

$$EGR = ([CO_2]_{int} - [CO_2]_{amb})/([CO_2]_{ext} - [CO_2]_{amb}) \quad (1)$$

EGR: EGR ratio
$[CO_2]_{int}$: $CO_2$ concentration at intake air side
$[CO_2]_{ext}$: $CO_2$ concentration at exhaust gas side
$[CO_2]_{amb}$: $CO_2$ concentration in inhaled fresh air (atmosphere)

If $[CO_2]_{amb}$ is ignored, the EGR ratio can be calculated by the following expression (2).

$$EGR = [CO_2]_{int}/[CO_2]_{ext} \quad (2)$$

At this time, in order to eliminate an influence of interference due to water on the $CO_2$ concentration, a dehumidifier is arranged in mid-course from a sample point to a $CO_2$ analyzer so that the sample gas is dehumidified (non-patent document 1).

PRIOR ART DOCUMENTS

Patent Document

Patent document 1: Japan patent laid-open number 2008-69690

Non Patent Document

Non patent document 1: Engine emission measurement handbook page 132~page 133 (Sankaido Publishing Co., Ltd.)

DISCLOSURE OF THE INVENTION

Problems to be Solved by the Invention

However, with the above-mentioned arrangement, since the EGR ratio measuring device requires a cooler and a pipe for dehumidification, not only the device becomes bulky but also the pipe length from the sample point to the $CO_2$ analyzer becomes long, thereby aggravating the measurement responsiveness. As a result, the transient error is easily generated between the measured value of the $CO_2$ concentration at the intake air side and the measured value of the $CO_2$ concentration at the exhaust gas side, which exerts a harmful influence on the measurement accuracy. In addition, it might also happen that $CO_2$ in the gas dissolves into the water discharged at a time of dehumidification, resulting in the measurement error.

The present claimed invention is to solve all of the problems and a main object of this invention is to improve the measurement accuracy of the EGR ratio and to downsize the device and to save labor.

Means to Solve the Problems

More specifically, an EGR ratio measuring device in accordance with this invention is to measure an EGR ratio of an internal combustion engine based on a concentration of $CO_2$ in an intake air introduced into a combustion chamber of the internal combustion engine and a concentration of $CO_2$ in an exhaust gas discharged from the combustion chamber, and is characterized by comprising a pair of nondispersive infrared gas analyzers that have a function of correcting a water influence and that can measure a concentration of $CO_2$ in a gas containing water, an intake air introduction line that is connected to an intake air pipe of the internal combustion engine and that introduces a part of the intake air into one of the nondispersive infrared gas analyzers without removing the water, an exhaust gas introduction line that is connected to an exhaust gas pipe of the internal combustion engine and that introduces a part of the exhaust gas into the other nondispersive infrared gas analyzer without removing the water, and a temperature adjusting mechanism that keeps a temperature of whole of the intake air introduction line and the exhaust gas introduction line and a temperature of the nondispersive infrared gas analyzers so as not to condense dew and that keeps the temperature of the nondispersive infrared gas analyzer higher than the temperature of the intake air introduction line and the temperature of the exhaust gas introduction line.

In addition, in order to make it possible to output an accurate measurement value directly without conducting a response speed correction even though at a time of transient measurement, it is preferable that a configuration of the intake air introduction line including a flow channel length is set to be substantially the same as a configuration of the exhaust gas introduction line including a flow channel length.

Effect of the Invention

In accordance with this invention, since all of the part from the sample point to the analyzers is kept at a temperature so that dew condensation is prevented, there would be no measurement error of the $CO_2$ concentration due to dew condensation. In addition, since a water removing mechanism such as a dehumidifier or a drain is not arranged at all on the intake air introduction line from the sample point of the intake air pipe to the nondispersive infrared gas analyzer as being a $CO_2$ concentration measuring device and the exhaust gas introduction line from the sample point of the exhaust gas pipe to the nondispersive infrared gas analyzer, it is possible to shorten the flow channel length as much as possible so that a responsiveness can be improved.

As a result, it is possible to obtain the concentration of $CO_2$ in the exhaust gas and the concentration of $CO_2$ in the intake air simultaneously without any transient error so that the measurement accuracy of the EGR ratio can be improved. In addition, since the flow channel length is shortened, the arrangement can contribute to downsizing and weight saving. Furthermore, since the sample flow rate can be reduced, a volume of a pump can also be lessened, thereby promoting cost reduction.

In addition, with an arrangement wherein the temperature is simply raised, contamination might be generated for the nondispersive infrared gas analyzer in detecting various component, however, with this invention, since the temperature of the analyzer alone is set higher than the other part, the measurement accuracy can be secured with avoiding these problems.

BEST MODES OF EMBODYING THE INVENTION

One embodiment of this invention will be explained with reference to drawings.

Figure 1:
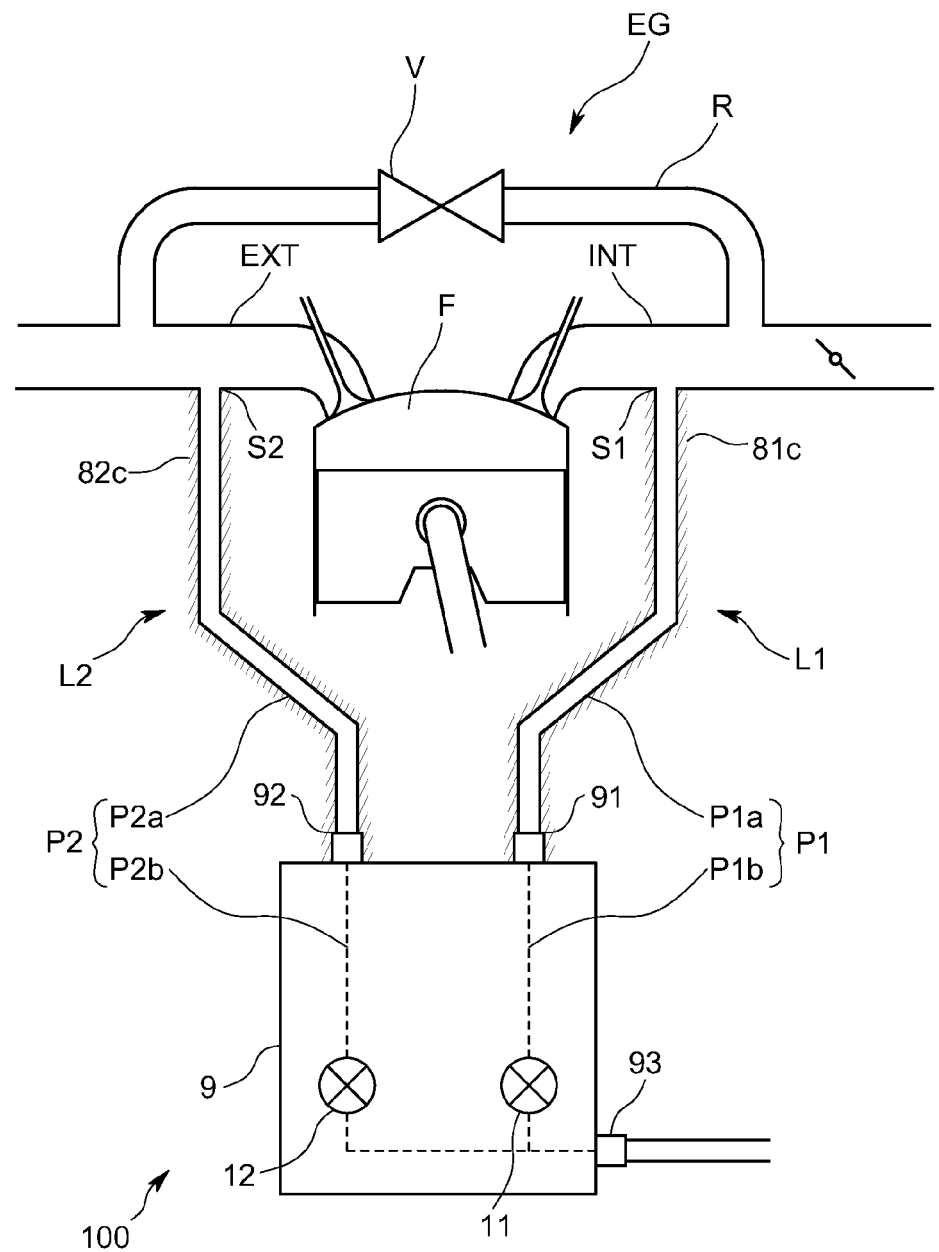
FIG. 1 is a whole pattern view of an EGR ratio measuring device in accordance with one embodiment of this invention.

As shown in FIG. 1, an EGR ratio measuring device 100 in accordance with this embodiment measures an EGR ratio of an internal combustion engine EG based on a concentration of $CO_2$ in an intake air introduced into a combustion chamber F of the internal combustion engine EG and a concentration of $CO_2$ in an exhaust gas discharged from the combustion chamber F.

More concretely, the EGR ratio measuring device 100 comprises a first analyzer 11 that measures the concentration of $CO_2$ in the intake air and a second analyzer 12 that measures the concentration of $CO_2$ in the exhaust gas, an intake air introduction line L1 that is connected to an intake air pipe INT of the internal combustion engine EG and that introduces a part of the intake air into the first analyzer 11, an exhaust gas introduction line L2 that is connected to an exhaust gas pipe EXT of the internal combustion engine EG and that introduces a part of the exhaust gas into the second analyzer 12, and temperature adjusting mechanisms 81a~81c, 82a~82c each of which keeps a temperature of the introduction lines L1, L2 and the analyzers 11, 12 over a certain temperature.

Each component will be explained.

Figure 2:
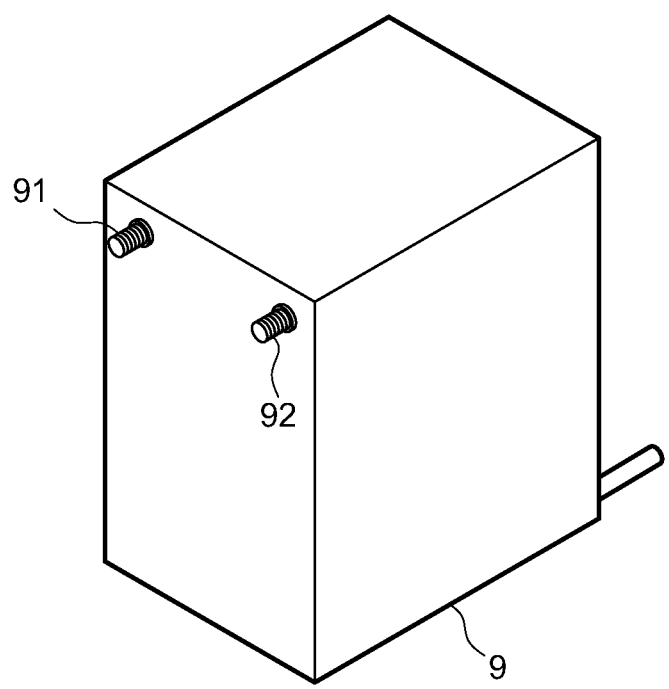
FIG. 2 is an external view of a housing of the device of this embodiment.
Figure 3:
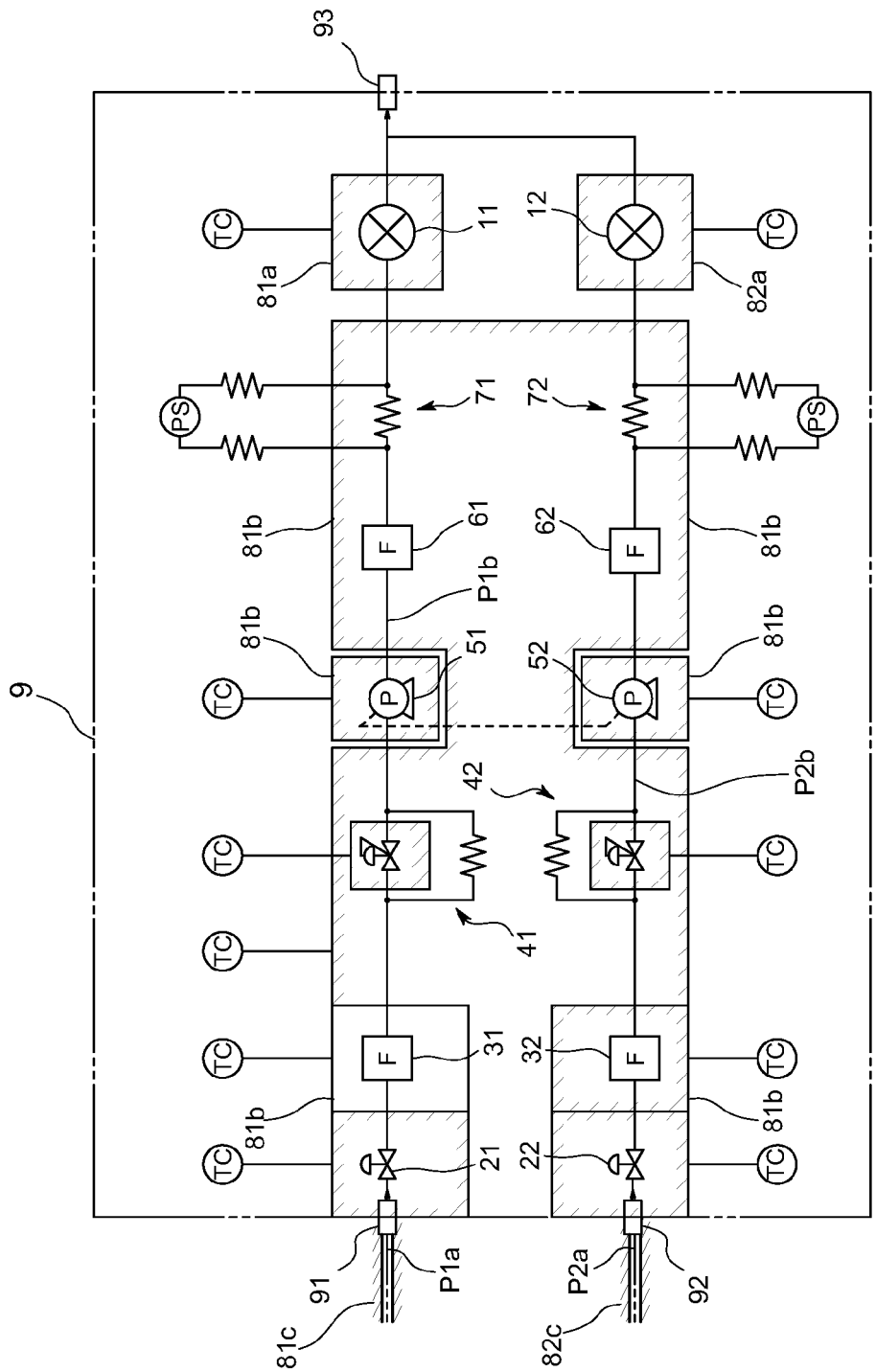
FIG. 3 is a hydraulic circuit diagram in the housing of this embodiment.
Figure 4:
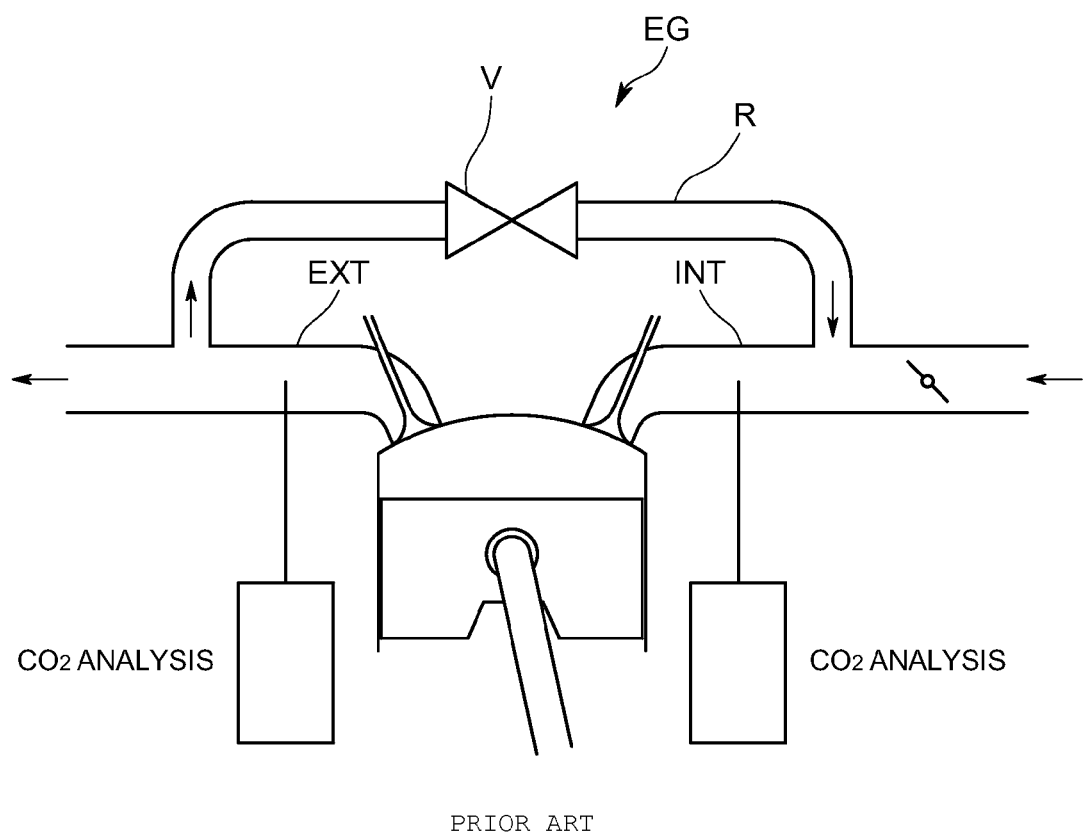
FIG. 4 is a pattern view showing a method for measuring an EGR ratio.

The first analyzer 11 and the second analyzer 12 are, as shown in FIG. 1, FIG. 2, FIG. 3, housed in a hollow cuboid housing 9. As shown in the Japan patent laid-open number 2003-172700, each of the first analyzer 11 and the second analyzer 12 is a nondispersive infrared gas analyzer that measures an optical absorption intensity in a characteristic absorption band of, for example, each CO, $CO_2$, $H_2O$, and calculates the concentration of CO and $CO_2$ by conducting a correction of a water interference influence and a water coexistence influence on the measured optical absorption intensity. Each of the first and the second analyzers 11, 12 has a characteristics of being able to calculate the concentration of CO and $CO_2$ with high accuracy even though the gas contains water (a WET gas).

The intake air introduction line L1 comprises a pipe P1 that connects a sample point S1 set at a downstream of a junction of a circulation path R and the intake air pipe INT with the first analyzer 11, and various fluid equipment arranged on the pipe P1.

The pipe P1 comprises an external pipe P1a that connects the sample point S1 with an intake air introduction port 91 arranged on the housing 9, and an internal pipe P1b that connects the intake air introduction port 91 with the first analyzer 11.

The fluid equipment is arranged on the internal pipe P1b and housed in the housing 9. In this embodiment, as shown in FIG. 3, an open/close valve 21, an oil removing filter 31 to remove oil in the gas, a regulator 41, a suction pump 51, a filter 61 and a flow meter 71 are arranged in this order from the upstream. The regulator 41 is to stabilize a load on the pump 51 so as to keep a constant flow ratio.

The exhaust gas introduction line L2 has the same configuration as that of the intake air introduction line L1, and comprises a pipe P2 that connects a sample point S2 set at the upstream of a junction of the circulation path R and the exhaust gas pipe EXT with the second analyzer 12, and various fluid equipment arranged on the pipe P2.

Similar to the intake air introduction line L1, the pipe P2 comprises an external pipe P2a that connects the sample point S2 with the exhaust gas introduction port 92 arranged on the housing 9, and an internal pipe P2b that connects the exhaust gas introduction port 92 with the second analyzer 12.

Similar to the intake air introduction line L1, the fluid equipment is also arranged on the internal pipe P2b and housed in the housing 9. Concretely, an open/close valve 22, an oil removing filter 32 to remove oil in the gas, a regulator 42, a suction pump 52, a filter 62 and a flow meter 72 are arranged in this order from the upstream.

In this embodiment, each of an internal pipe length, an external pipe length and a pipe diameter of the intake air introduction line L1 is set to be equal to that of the exhaust gas introduction line L2 respectively, and each fluid equipment for the intake air introduction line L1 uses the same fluid equipment for the exhaust gas introduction line L2 so that the flow rate of the gas introduced into each analyzer 11, 12 becomes generally the same.

Furthermore, all of the whole length of the pipes P1, P2, and the fluid equipment 21~71, 22~72 are kept at about 90° C. at which temperature dew is not condensed by the temperature adjusting mechanisms 81, 81c, 82b, 82c having a heater or the like. The analyzers 11, 12 are also kept at a temperature at which temperature dew is not condensed by the temperature adjusting mechanisms 81a, 82a and the temperature of the analyzers 11, 12 is about 120° C. that is different from and a little higher than the temperature of the pipes P1, P2.

In accordance with the EGR measuring device having this arrangement, since a water removing mechanism such as a dehumidifier or a drain is not at all arranged on the intake air introduction line L1 from the sample point S1 of the intake air pipe INT to the analyzer 11 and the exhaust gas introduction line L2 from the sample point S2 of the exhaust gas pipe EXT to the analyzer 12, it is possible to shorten the flow channel length as much as possible so that a responsiveness can be improved and the EGR measurement accuracy especially in a transient state (while the engine is not in a steady state) can be improved. In addition, since the pipe length and the pipe diameter of the intake air introduction line is set to be generally equal to those of the exhaust gas introduction line, it is possible to output an accurate measurement value directly without conducting a response speed correction even though in a transient state.

In addition, if due is condensed accidentally in a mid-course of the introduction lines L1, L2, the concentration of $CO_2$ fluctuates in the introduction lines L1, L2 so that it becomes difficult to conduct the measurement of $CO_2$ concentration accurately. However, with this arrangement, since the temperature of the entire length of the introduction lines L1, L2 is adjusted not to condense dew, there would be no problem in conducting the measurement of the $CO_2$ concentration accurately.

In addition, since the temperature of the analyzer 11, 12 is set to be higher than the other part, it is possible to securely prevent the analyzer 11, 12 from being contaminated.

The present claimed invention is not limited to the above-mentioned embodiment and may be variously modified without departing from a spirit of the invention.

EXPLANATION OF CODES

EG . . . internal combustion engine
F . . . combustion chamber
INT . . . intake air pipe
EXT . . . exhaust gas pipe
100 . . . EGR ratio measuring device
11, 12 . . . nondispersive infrared gas analyzer
L1 . . . intake air introduction line
L2 . . . exhaust gas introduction line
81a~81c, 82a~82c . . . temperature adjusting mechanism

The invention claimed is:
1. An EGR ratio measuring device to measure an EGR ratio of an internal combustion engine based on a concentration of $CO_2$ in an intake air introduced into a combustion chamber of the internal combustion engine and a concentration of $CO_2$ in an exhaust gas discharged from the combustion chamber, and comprising a pair of nondispersive infrared gas analyzers that have a function of correcting a water influence and that can measure a concentration of $CO_2$ in a gas containing water, an intake air introduction line that is connected to an intake air pipe of the internal combustion engine and that introduces a part of the intake air into one of the nondispersive infrared gas analyzers without removing the water, an exhaust gas introduction line that is connected to an exhaust gas pipe of the internal combustion engine and that introduces a part of the exhaust gas into the other nondispersive infrared gas analyzer without removing the water, and a temperature adjusting mechanism that keeps a temperature of whole of the intake air introduction line and the exhaust gas introduction line and a temperature of the nondispersive infrared gas analyzers so as not to condense dew and that keeps the temperature of the nondispersive infrared gas analyzer higher than the temperature of the intake air introduction line and the temperature of the exhaust gas introduction line.

2. The EGR ratio measuring device described in claim 1, wherein
a configuration of the intake air introduction line including a flow channel length is set to be substantially the same as a configuration of the exhaust gas introduction line including a flow channel length.

* * * * *